United States Patent [19]

Cassady et al.

[11] Patent Number: 5,646,320

[45] Date of Patent: Jul. 8, 1997

[54] PROCESS FOR MAKING ISETHIONATE ESTER SALTS

[75] Inventors: Timothy John Cassady, Hamilton; Norman Milstein, Montgomery, both of Ohio; Richard P. Crews, Simpsonville, S.C.

[73] Assignee: Henkel Corporation, Plymouth Meeting, Pa.

[21] Appl. No.: 260,932

[22] Filed: Jun. 16, 1994

Related U.S. Application Data

[63] Continuation-in-part of Ser. No. 144,266, Oct. 28, 1993, abandoned.

[51] Int. Cl.$^6$ ............................................... C07C 51/00
[52] U.S. Cl. ..................... 554/149; 554/92; 554/97; 554/154; 554/155; 554/156; 554/158; 562/120
[58] Field of Search ......................... 554/92, 97, 149, 554/154, 155, 156, 158; 562/120

[56] References Cited

U.S. PATENT DOCUMENTS

| | | | |
|---|---|---|---|
| 2,597,696 | 5/1952 | Anthes et al. | 260/513 |
| 2,810,747 | 10/1957 | Sexton et al. | 260/513 |
| 2,820,818 | 1/1958 | Sexton et al. | 260/513 |
| 2,894,912 | 7/1959 | Geitz | 252/121 |
| 3,004,049 | 10/1961 | Schenck | 260/400 |
| 3,094,555 | 6/1963 | Lamberti et al. | 260/513 |
| 3,151,136 | 9/1964 | Koczorowski et al. | 260/400 |
| 3,376,229 | 4/1968 | Haass et al. | 252/117 |
| 4,003,925 | 1/1977 | Lamberti et al. | 260/513 R |
| 4,180,470 | 12/1979 | Tokosh et al. | 252/121 |
| 4,206,069 | 6/1980 | Borrello | 252/122 |
| 4,405,526 | 9/1983 | Lamberti et al. | 260/400 |
| 4,476,055 | 10/1984 | Du Vernet | 260/400 |
| 4,515,721 | 5/1985 | Login et al. | 260/400 |
| 4,536,338 | 8/1985 | Urban et al. | 260/400 |
| 4,663,070 | 5/1987 | Dobrovoiny et al. | 252/121 |
| 4,695,395 | 9/1987 | Caswell et al. | 252/121 |
| 4,851,147 | 7/1989 | Esposito et al. | 252/108 |
| 4,954,281 | 9/1990 | Resch | 252/107 |
| 4,954,282 | 9/1990 | Rys | 252/117 |
| 4,963,284 | 10/1990 | Novakovic et al. | 252/108 |
| 5,030,376 | 7/1991 | Lee et al. | 252/108 |
| 5,041,233 | 8/1991 | Kutny et al. | 252/121 |
| 5,132,037 | 7/1992 | Greene et al. | 252/108 |
| 5,185,101 | 2/1993 | Weipert | 252/554 |

FOREIGN PATENT DOCUMENTS

| | | |
|---|---|---|
| 0459769 | 12/1991 | European Pat. Off. . |
| 0813593 | 8/1960 | United Kingdom . |
| 1059984 | 2/1967 | United Kingdom . |

OTHER PUBLICATIONS

CA 51: 16514e (1957).
Nature 160, 795–6 (1947).

*Primary Examiner*—Debareh D. Carr
*Attorney, Agent, or Firm*—Wayne C. Jaeschke; John E. Drach; Henry E. Millson, Jr.

[57] ABSTRACT

Fatty acid esters of isethionate salts are made by reacting ethylene oxide and a bisulfite salt, that may be made in situ, in aqueous ammonia while maintaining (1) the pH in the range of about 5.5 to about 6.5 and (2) the temperature in the range of 25° C. to 85° C. to form an isethionate salt. The isethionate salt is then esterified with a fatty acid to produce a product having little or no unwanted fatty acid esters of ethylene glycol.

18 Claims, No Drawings

PROCESS FOR MAKING ISETHIONATE ESTER SALTS

RELATED APPLICATION

This application is a continuation-in-part of application Serial No. 08/144,266, filed Oct. 28, 1993, the entire contents of which are incoporated herein by reference, now abandoned.

BACKGROUND OF THE INVENTION

1. Field of the Invention

This invention relates to a process for making salts and fatty acid esters of isethionic acid, which minimizes the formation of unwanted by-products. It also relates to the ester compositions produced.

2. Description of the Related Art

Sodium, other alkali metal, and ammonium salts of the fatty acid esters of isethionic acid (2-hydroxyethanesulfonic acid) are useful as mild, foaming surfactants. These isethionate ester salts are usually manufactured by first forming an isethionate salt by reaction of ethylene oxide with an aqueous solution of a bisulfite salt such as sodium bisulfite or ammonium bisulfite. The free alcohol functionality of the isethionate salt is then esterified with a fatty acid to produce a fatty acid ester of the isethionate salt.

One of the principal problems encountered in this process is the production of ethylene glycol as a by-product during the reaction of ethylene oxide and the bisulfite salt. The ethylene glycol thus formed subsequently reacts with the fatty acid in the second step of the process, resulting in the formation of mono- and di-esters of ethylene glycol which are only partially soluble in aqueous-based formulations of the acyl-isethionate products wherein the solids content is greater than 30% by weight. These partially soluble materials result in the formation of a hazy, aqueous product that contains fine solids which are difficult and costly to remove.

It would be advantageous to avoid the formation of the ethylene glycol fatty acid esters so that a clear aqueous product could be obtained without the need for additional processing steps which add to the cost of the product. The present invention is a method for making fatty acid esters of alkali metal and ammonium isethionates which minimizes the formation of ethylene glycol, which in turn lowers the chance that fatty acid esters of ethylene glycol will form and contaminate the final product.

SUMMARY OF THE INVENTION

It has been discovered surprisingly that a fatty acid ester of an isethionate salt, wherein the amount of mono- and di-fatty acid esters of ethylene glycol are held to a minimum, can be made by a two step process. In the first step, ethylene oxide and a bisulfite salt are reacted in an aqueous solution while the pH of the solution is maintained in the range of from 5.5 to 6.5 and the temperature of the solution is maintained in the range of from 25° C. to 85° C. The control of the pH and the temperature in this first step of the process minimizes the formation of ethylene glycol while maximizing the amount of the desired product, which is an isethionate salt. The amount of ethylene glycol formed is less than 0.85% based on the weight of a 60% solution of the isethionate salt.

A fatty acid ester of the isethionate salt is then formed in the second step by reaction of the isethionate salt with a fatty acid. Because the amount of ethylene glycol formed is equal to or less than 0.85% by weight of a 60% aqueous solution of the esterified isethionate salt, the amount of mono- and di-fatty acid esters of ethylene glycol formed in the competing esterification of ethylene glycol by the fatty acid is low enough so that a clear aqueous product at ambient temperature is obtained.

DESCRIPTION OF THE PREFERRED EMBODIMENTS

Other than in the operating examples, or where otherwise indicated, all numbers expressing quantities of ingredients or reaction conditions used herein are to be understood as modified in all instances by the term "about". In addition, all parts and percentages are by weight, and all temperatures are in degrees Celsius, unless expressly stated to be otherwise. When parts by weight or percentages are reported for a solution of a solute that is solid when dry, those parts or percentages based on the solution refer to the solution on an "as is" basis, again unless expressly stated to be otherwise.

In the process according to the invention, ethylene oxide and a bisulfite salt are reacted in aqueous solution to form an isethionate salt which is a salt of 2-hydroxyethanesulfonic acid. The bisulfite salt can be introduced into the reaction as the salt itself such as by adding sodium bisulfite or it may be made in situ such as by the reaction of aqueous ammonia (ammonium hydroxide) and sulfur dioxide.

In a preferred embodiment of the process according to the invention, ammonium bisulfite is reacted with ethylene oxide. Ammonium bisulfite can be made by any method known to those skilled in the art. Most preferably, the ammonium bisulfite is made in situ by reaction of aqueous ammonia (ammonium hydroxide) and sulfur dioxide. In general, the ethylene oxide is added to the aqueous solution of ammonia incrementally and alternately with the sulfur dioxide at such a rate that the reaction temperature is maintained in the range of from 25° C. to 85° C. and the pH is maintained in the range of from 5.5 to 6.5. Control of the reaction temperature in the 25° C. to 85° C. range and of the pH in the 5.5 to 6.5 range are essential features of the process according to the invention.

The amount of ethylene glycol formed in the process according to the invention is a function of the combination of the reaction temperature and the pH. When the reaction temperature is maintained in the 25° C. to 85° C. range and pH is maintained in the 5.5 to 6.5 range, the maximum amount of ethylene glycol formed is 0.85% based on the weight of a 60% aqueous solution of the isethionate salt. When the reaction temperature is maintained in the 60° C. to 65° C. range and the pH is maintained in the 5.8 to 6.2 range, the maximum amount of ethylene glycol formed is 0.50% based on the weight of a 60% aqueous solution of the isethionate salt. Thus, it is preferred to maintain the reaction temperature in the 60° C. to 65° C. range and the pH in the 5.8 to 6.2 range.

The pH can be controlled by addition of aqueous base, preferably aqueous ammonia, to the reaction mixture. To make the reaction mixture more acidic, that is, have a lower pH value, the addition of citric acid is preferred. The reaction temperature can be controlled by adjusting the addition rate of ethylene oxide and/or sulfur dioxide or by cooling the reaction mixture by any heat exchange means known to those skilled in the art or by a combination of an adjustment of the ethylene oxide/sulfur dioxide addition rates and by using a heat exchange means.

While any saturated or unsaturated carboxylic acid can be used in the process according to the invention, carboxylic acids traditionally classified as fatty acids, especially those having from 6 to 22 carbon atoms, are preferred. Fatty acids having from 8 to 18 carbon atoms are most preferred. The fatty acid can be a mixture of fatty acids such as those obtained from naturally occurring fats and oils. A preferred mixture of fatty acids is a simulated coconut oil fatty acid composition comprised approximately of (weight %) 6% $C_{10}$, 49–51% $C_{12}$, 18–19% $C_{14}$, 9–10% $C_{16}$, 7% $C_{1:0}$, and 1–3% $C_{18:1}$ fatty acids, that is a proprietary product of Henkel Corporation, Emery Group, Cincinnati, Ohio.

Generally, the fatty acids from coconut oils give satisfactory results. Like all natural products, coconut oils differ in composition depending on the source, weather, the season, and like factors.

TABLE I

COMPOSITION OF FATTY ACIDS OF COCONUT OIL

| Comp'n. of fatty acids, wt. % of | (a) | (b) | (c) |
|---|---|---|---|
| Saturated | | | |
| total fatty acids | | | |
| Caprylic | 9.7 | 8.2 | 6.8 |
| Lauric | 44.3 | 52.1 | 46.4 |
| Myristic | 15.9 | 13.3 | 18.0 |
| Palmitic | 9.6 | 7.6 | 9.0 |
| Stearic | 3.2 | 2.1 | 1.0 |
| Arachidic | Trace | Trace | |
| Unsaturated | | | |
| Hexadecenoic | — | None | — |
| Oleic | 6.3 | 5.5 | 7.6 |
| Linoleic | 1.5 | 2.3 | 1.6 |

<sup>a</sup>Oil from copra from South Sea Islands.
<sup>b</sup>Oil from copra from Hainan Island, S. China.
<sup>c</sup>Commercial oil from American refiner (California); probably from Philippine copra.

Source: *Handbook of Food and Agriculture*, Reinhold Publishing Corporation, New York, 1955, page 492.

In addition to coconut oil, palm-kernel and palm oil may be used, although if palm oil is used, it is preferred that it be used in admixture with one of the other two. Tallow fatty acids can also be used, but preferably as a diluent for coconut oil.

Generally, the term "coconut oil" is used here to refer to fatty acid mixtures having an approximate carbon chain length distribute that provides a profile high in lauric acid, $C_{12}$, 48–52%; myristic acid, $C_{14}$, 16–20%; and relatively minor percentages of the other fatty acids. Other fatty acid sources, having similar carbon chain length distributions, are intended to be included within the term "coconut oil".

When the process according to the invention is used to manufacture ammonium cocoyl isethionate, a composition may be obtained from practicing one embodiment of the invention, comprising: (a) ammonium cocoyl isethionate; (b) ammonium isethionate; (c) coconut fatty acid; (d) triethanolamine; and (e) water, is realized which provides a synthetic detergent solution useful for the manufacture of personal care products such as shampoo, liquid hand soap, shower gel, personal cleansing bars, and the like.

The presence of triethanolamine in the final product composition generally means that triethanolamine was added, at the conclusion of the reaction, to neutralize the acidic catalyst. It is also possible to use ammonia as a neutralizing agent, and to make final adjustments to the pH, to be in the preferred range of 6.6–6.8, by additions of ammonia or citric acid, depending upon the pH adjustment that is desired. Generally the solids content in the final product composition should be in the range from 30–33%, and this value also may be adjusted either by adding water or distilling off water.

It is also possible to use other neutralizing agents, such as sodium hydroxide, potassium hydroxide, and the basic amines, particularly the more basic tertiary amines such as triethanolamine. Since generally triethanolamine imparts special properties to compositions comprising the coconut oil ester of an isethionic acid salt, it may be used in conjunction with another base such as ammonium hydroxide. For example, triethanolamine may affect the visual characteristics of the final composition, expecially with respect to translucency.

Hydrogen peroxide may also be added, for several purposes. When added, it converts the hypophosphorous acid, that may have been used as the catalyst or as a part of the catalyst, and its ammonium salts, into phosphoric acid and its ammonium salts. The addition of hydrogen peroxide improves both the color and odor of the product solutions. When ammonia is used to neutralize the catalyst, and when hydrogen peroxide is used to convert the hypophosphorous acid and its ammonium salts into phosphoric acid and its ammonium salts, a color stable ammonium cocoyl isethionate solution may be obtained with 30–32% solids, an activity of 24–29%, and a Gardner 1–2 color.

The following examples are meant to illustrate but not to limit the invention.

Example 1

Preparation of Ammonium Isethionate

A reactor was charged with 29 parts of water and evacuated to a pressure of 50–75 mm Hg. The reactor was repressurized with nitrogen to a pressure of 20 psig and the reevacuated to a pressure of 50–75 mm Hg. About 25.5 parts of 28% aqueous ammonium hydroxide were then added and the reactor was pressurized to 6 psig with nitrogen.

The first of a series of sulfur dioxide-ethylene oxide addition cycles was commenced by adding a portion of the required 26.7 parts of sulfur dioxide at a rate such that the reaction temperature was maintained in the 60°–70° C. range and in such an amount that the pH reached a value of 5.7–5.8. If, during the sulfur dioxide addition, the pH dropped below 5.7, it was adjusted back to 5.7 by addition of 28% aqueous ammonium hydroxide. After the sulfur dioxide addition was complete, the reaction mixture was stirred for 10 minutes at 60°–70° C. The reactor was then purged to 30 psig with nitrogen and vented back to 6 psig whereupon a portion of 18.5 parts of ethylene oxide were added while the temperature was maintained at 60°–65° C. and until the pH rose to 6.2. The total pressure over the reaction was never allowed to exceed 50 psig.

After reaching a pH of 6.2 by the addition of a portion of the ethylene oxide, successive sulfur dioxide-ethylene oxide addition cycles were carried out during each of which the reaction temperature was maintained in the 60°–65° C. range and the pH was maintained in the 5.8–6.2 range until all of the sulfur dioxide and ethylene oxide were added. The pH was maintained in the 5.8–6.2 range if necessary, by the addition of 28% aqueous ammonium hydroxide. The alternate additions of sulfur dioxide and ethylene oxide were continued until the sum of the ammonium sulfite and ammonium bisulfite equaled 0.25% to 0.05% as measured by iodometric titration (iodine-thiosulfate). After these levels were reached, an amount of 35% hydrogen peroxide sufficient to convert the remaining ammonium sulfite and ammonium bisulfite to ammonium sulfate and ammonium bisulfate was added.

The effect of reaction temperature and pH on the ethylene glycol content of ammonium isethionate is shown in Table I, which is a listing of data from 14 reactions carried out according to the method set forth in this Example 1. The data show that when the pH of the reaction solution is maintained in the range of from 5.5 to 6.5 and the temperature of the solution is maintained in the range of from 25° C. to 85° C., the amount of ethylene glycol formed is less than 0.85% based on the weight of a 60% aqueous solution of the isethionate salt.

TABLE 1

| # | pH | Temp[1] | % EG[2] | Reactant[3] | $EO/SO_2$[4] |
|---|---|---|---|---|---|
| 1 | 5.0–6.5 | 83–87 | 1.2 | $NH_4SO_3H$ | — |
| 2 | 5.0–6.6 | 83–87 | 1.3 | $NH_4SO_3H$ | — |
| 3 | 5.6–6.2 | 84 | 0.82 | $NH_4OH$ | 1.016 |
| 4 | 5.3–6.5 | 84–85 | 1.36 | $NH_4OH$ | — |
| 5 | 5.3–6.2 | 84–85 | 0.93 | $NH_4OH$ | 1.00 |
| 6 | 5.8–6.2 | 83–84 | 0.62 | $NH_4OH$ | 1.02 |
| 7 | 5.8–6.1 | 83–84 | 0.65 | $NH_4OH$ | 1.00 |
| 8 | 5.8–6.1 | 83–85 | 0.66 | $NH_4OH$ | 1.00 |
| 9 | 5.9–6.2 | 83–85 | 0.64 | $NH_4OH$ | — |
| 10 | 5.9–6.2 | 66 | 0.46 | $NH_4OH$ | 1.00 |
| 11 | 5.8–6.1 | 61–62 | 0.40 | $NH_4OH$ | 1.00 |
| 12 | 5.8–6.2 | 65–66 | 0.43 | $NH_4OH$ | 1.00 |
| 13 | 5.8–6.2 | 75–76 | 0.56 | $NH_4OH$ | 1.02 |
| 14 | 5.8–6.2 | 70 | 0.52 | $NH_4OH$ | 1.01 |

[1]- ethylene oxide addition temperature (°C.)
[2]- Wt. % ethylene glycol formed
[3]- $NH_4SO_3H$ -added as ammonium bisulfite and then reacted with ethylene oxide
$NH_4OH$ - ammonium bisulfite made in situ by reaction of $NH_4OH + SO_2$
[4]- mole ratio of $EO/SO_2$ When $NH_4SO_3H$ made in situ Example 2

Preparation of Ammonium Cocoyl Isethionate (ACI)

A reactor was charged with 329 lbs. of Henkel's simulated coconut fatty acid (6% $C_{10}$, 49–51% $C_{12}$, 18–19% $C_{14}$, 9–10% $C_{16}$, 7% $C_{18:0}$, 1–3% $C_{18:1}$, fatty acids), 370 lbs. of the ammonium isethionate solution from Example 1 (59% aqueous solution), 251 grams (0.55 lbs.) of 99% methanesulfonic acid, and 258 grams (0.55 lbs.) of 50% hypophosphorous acid. The pressure was reduced to 25 inches of vacuum and the reactor was heated to 130° C.–150° C. Water, which began to distill over at 700°–80° C., was continuously removed until the theoretical amount of water from the ammonium isethionate solution, 151 lbs., was collected. The vacuum was then decreased to 15 inches and the temperature was increased to 175°±5° C. The mixture was held at 175°±5° C. and 15 inches of vacuum for 4 hours. The vacuum was increased to 25 inches and the temperature was then increased to 190° C. After the temperature reached 190° C., the mixture was held at 190° C. and 25 inches of vacuum for 3 hours.

The reaction mixture was then sampled and the conversion to ammonium cocoyl isethionate was assessed by Epton titration (Nature 160, 795–6 (1947); Trans. Faraday So., 44, 226–30 (1948), the entire contents of which are incorporated herein by reference, and $^1H$ NMR analysis (see Example 4). The reaction mixture was maintained at 190° C. and 2 inches of vacuum until the Epton titration indicated sufficient conversion to ammonium cocoyl isethionate (this is indicated by Epton titration values of from 81–89%) at which time 12.3 lbs. of triethanolamine in 992 lbs. of water were rapidly added to lower the temperature to 50° C. The pH was adjusted to 6.6–6.8 with further additions of triethanolamine and the solids content was adjusted to 30–33% by adding water.

The product produced in this example has an odor that is characteristic of the presence of hypophosphorous acid and ammonium hypophosphite. To improve the odor, an amount of 35% hydrogen peroxide, equivalent to at least 0.02% by weight of the ammonium cocoyl isethionate solution at 30–32% solids, was added. The addition of hydrogen peroxide immediately improved the odor by converting the hypophosphorous acid and ammonium hypophosphite into phosphoric acid and ammonium phosphate salts. The amount of hydrogen peroxide which can be added to imporve the color will typiclly range from 0.02% to about 0.3%. The preferred amount is from 0.02% to 0.1% by weight of the ammonium cocoyl isethionate solution at 30–32% solids.

Hydrogen peroxide also gradually improves the color of the ACI. When the reaction is conducted in a stainless steel reactor, from time to time it has been found that the color degrades, after an initial color improvement. Through color stability testing of ACI solutions, prepared under different respective reaction conditions, it has been determined that hydrogen peroxide has an adverse effect on the color of ACI solutions that are neutralized using triethanolomine. Accordingly, a process modification was designed, to eliminate the color stability problem. This process modification is described in the following Example 3.

Example 3

Preparation of Ammonium Cocoyl Isethionate (ACI) Using Ammonium Hydroxide Neutralization A reactor was charged with: 329 lbs. of coconut fatty acid, the Henkel simulated coconut fatty acid product referred to in Example 2, but from a different batch having a slightly different fatty acid profile; 370 lbs. of the ammonium isethionate solution from Example 1, at 59.05% concentration by weight; 251 g. (0.55 lbs.) of 99% methanesulfonic acid; and 248 g. (0.55 lbs.) of 50% hypophosphorous acid. Nitrogen pressure was applied to the bottom valve of the reactor, to minimize or eliminate the possibility of air leaking into the reaction mixture. Above surface and subsurface nitrogen flow into the reaction mixture was established to facilitate the removal of water and to maintain a nitrogen atmosphere in order to maintain a light product color due to the absence of air or oxygen.

The pressure was reduced to 15 to 25 inches Hg of vacuum, and the reactor was heated to 130°–150° C. Water began to distill over at 70°–80° C., and was continuously removed until the theoretical amount of water from the ammonium isethionate solution, 151 lbs., had been collected.

The vacuum was then decreased to 15 inches Hg and the temperature was increased to 175°±5° C. The mixture was held at this temperature and at 15 inches Hg of vacuum for 4 hours. The vacuum was increased to 25 inches Hg, and the temperature was then increased to 190° C. After the temperature reached 190° C., the mixture was held at 190° C. and at 15 inches Hg for 3 hours. These reaction conditions minimized the formation of foam during the esterification of ammonium isethionate to form ammonium cocoyl isethionate by facilitating the removal of water from the viscous reaction mixture.

The reaction mixture was sampled and the conversion to ammonium cocoyl isethionate was assessed as in Example 2. The reaction mixture was maintained at 190° C. and 25 inches of Hg vacuum, until the Epton titration indicated sufficient conversion to ammonium cocoyl isethionate (this is indicated by Epton titration values of from 81% to 89%), at which time the mixture was cooled to a temperature of approximately 150° C.

A solution of 5.29 lbs. of ammonium hydroxide solution, containing 28% by weight ammonia, in 1,123 lbs. of water was rapidly added, to lower the temperature of the reaction mixture quickly to 50° C. The pH was adjusted to 6.6 to 6.8 with further additions of ammonia for a pH of less than 6.6, and with additions of citric acid for a pH greater than 6.8. The addition of citric acid also had a beneficial effect on the color stability of the ammonium cocoyl isethionate solution. In replicating this experiment, or in making some modification on it, the solids content of the reaction mixture is usually adjusted to 30–33% by adding water if the solids content is greater than 33%, and by distilling off water if the water content is less than 30%.

In order to convert the hypophosphorous acid and its ammonium salts into phosphoric acid and its ammonium salts, 1.65 lbs. of a 35% hydrogen peroxide was added. The addition of the hydrogen peroxide improved both the color and odor of the product solutions. The process resulted in the formation of a color stable ammonium cocoyl isethionate solution with a 30–32% solids content, an activity of 24–29%, and a Gardner 1–2 color.

The use of ammonium hydroxide to neutralize the reaction mixture is believed to have some advantages. It is completely compatible with the reaction mixture. Any by-products that it forms are also water soluble. Some reaction with any free fatty acid in the reaction mixture may occur, without any detrimental effect. Any excess of ammonium hydroxide tends to dissipate over a period of time. In addition, the reaction mixture is free of the triethanolamine that was used in Example 2, and thus there is no adverse effect upon the addition of hydrogen peroxide, as was the case with the color of the ACI solution in Example 2.

Example 4

$^1$H HMR Method for Composition of ACI

About 0.03 g of reaction mixture was dissolved in $d_6$-DMSO containing 0.5% (v/v) TMS and diluted to a volume of 1 ml. The 1 ml. The $^1$H NMR spectrum was recorded using a Varian United 400 NMR spectrometer operating at 400 MHz. The integration of the triplet at w 2.77 for the $CH_2$ group adjacent to the sulfonate group was used to indicate the relative molar amount of ACI. The integration of the triplet at w 2.67 for the $CH_2$ group adjacent to the carboxyl group was used to indicate the relative molar amount of fatty acid (RCOOH). The relative molar amounts are used to calculate a molar ratio of ACI to AI to fatty acid and then to calculate percentages by weight of these molecules in the product according to the following method. The mole ration of ACI, AI, and RCOOH is calculated by dividing the integration area for each of the peaks at w 2.77, w 2.67, and w 1.18 by the total of the integration areas for there three peaks. The % conversion of IA is then found by dividing the mole % of ACI by the sum of the mole % of AI and ACI.

CONCLUDING COMMENTS

When the ammonium hydroxide neutralization technique is used, as in Example 3, the composition of the reaction product comprises: (a) ammonium cocoyl isethionate; (b) ammonium isethionate; (c) coconut fatty acid; (d) any excess use of ammonium hydroxide; (e) ammonium products, such as ammonium-fatty acid reaction products; (f) water; and (g) catalyst.

This reaction mixture is a useful detergent addition or base for the manufacture of a cleansing product requiring a high degree of solubility for ingredients, such as, for example, shampoo, liquid hand soap, and the like.

The ammonium cocoyl isethionate is much more water soluble than the esters of either the sodium or potassium salts. The ester of the sodium salt in particular finds use in toilet soap bars where a hard bar is desirable. The potassium cocoyl isethionate, being more soluble than the corresponding ester of the sodium salt, is useful where the cleansing bar need not be as hard, or where a soap gel type of product is desired. The ammonium cocoyl isethionate is very soluble and therefore is a very attractive product for formulating shampoos.

While the invention is primarily concerned with the production of ammonium cocoyl isethionate, because of its desirable properties, the process is more generally useful. For example, the reaction between ethylene oxide and the bisulfite salt, under the conditions of the present invention as to temperature and pH, is useful for the production of the fatty acid esters of the alkali metal and alkaline earth metal salts, because of the inhibition or limited formation of undesired by-products, particularly ethylene glycol. Thus, the process of the invention is useful for the production of sodium cocoyl isethionate and potassium cocoyl isethionate, as well as other fatty acid esters of isethionate salts.

In addition, the fatty acids used in the invention are not confined to those obtained from coconut oil or those similar in fatty acid profile to coconut oil. The oils from palm oil, babassu oil, soybean oil, castor oil, tallow oil, whale and fish oil, grease, lard and mixtures of such oils, can all be used either as partial or complete replacements for coconut oil. However, the coconut oil esters of ammonium isethionate are generally preferred for formulating cleansing compositions that are to be used on the human skin.

The catalyst during esterification may be a conventional catalyst, generally acidic. The preferred catalyst is a mixture of hypophosphorous acid and methanesulfonic acid, but either of these works alone. For reducing the production of ethylene glycol, the important thing seems to be the observance of the pH limits and of the temperature limits.

When the process of the invention is used to produce isethionate esters other than ammonium cocoyl isethionate, the neutralizing agent added, to adjust the final pH to a desired value, generally should be a basic material corresponding to the base from which the isethionate salt is formed, but not necessarily. For example, when making sodium cocoyl isethionate according to the invention, ordinarily sodium hydroxide, bicarbonate, or carbonate would be a desirable neutralizing agent. The reaction product would therefore comprise: (a) sodium cocoyl isethionate; (b) sodium isethionate; (c) coconut oil fatty acids; (d) sodium coconut oil fatty acid soaps; (e) any unreacted sodium hydroxide, carbonate, or other basic form of sodium; (f) any unreacted catalyst; and (g) water. More broadly, the neutralizing agent can be a basic material that contains an alkali metal, an alkaline earth metal, or a basic amine or a substituted amine such as triethanolamine. Basic materials that are compatible with the ultimate end use should be used.

While the invention has been disclosed above by reference to the details of preferred embodiments of the invention, it is to be understood that such disclosure is intended in an illustrative, rather than in a limiting sense. It is contemplated that modifications may be made in the processes and compositions that are disclosed, within the spirit of this invention and the scope of the appended claims.

What is claimed is:

1. A process for making an aqueous solution of a fatty acid ester of an isethionate salt comprising the steps of: (1) reacting ethylene oxide and a bisulfite salt in an aqueous solution while (a) maintaining the pH in the range of from about 5.5 to about 6.5 by the controlled addition of an acid or base to the reaction mixture, and (b) maintaining the temperature in the range of from 25° C. to 85° C. to form an aqueous isethionate salt solution; and (2) reacting said isethionate salt in said aqueous solution with at least one fatty acid to produce an aqueous solution of a fatty acid ester of an isethionate salt having a content of fatty acid esters of ethylene glycol of less than 0.85% based on the weight of a 60% solution of the isethionate salt and wherein said aqueous solution resulting from step (2) is clear at ambient temperature.

2. The process of claim 1 wherein said bisulfite salt is sodium bisulfite, potassium bisulfite, or ammonium bisulfite.

3. The process of claim 2 wherein said fatty acid comprises a mixture of $C_6$–$C_{22}$ fatty acids.

4. The process of claim 3 wherein said fatty acid comprises a composition comprised of, on a weight percent basis, 6% $C_{10}$, 49–51% $C_{12}$, 18–19% $C_{14}$, 9–10% $C_{16}$, 7% $C_{18:0}$, and 1–3% $C_{18:1}$ fatty acids.

5. The process of claim 1 wherein step (2) is carried out in the presence of a catalyst comprised of methanesulfonic acid and hypophosphorous acid.

6. The process of claim 1 wherein in step (1) said pH range is maintained in the range of from about 5.8 to about 6.2 and said temperature range is maintained in the range of from about 60° C. to about 65° C.

7. The process of claim 1 comprising the additional step of neutralizing the aqueous reaction mixture from step (2) if necessary to get a pH in the range of 6.6 to 6.8 using a basic material selected from the group consisting of triethanolamine and ammonium hydroxide.

8. The process of claim 7 wherein said bisulfite salt comprises ammonium bisulfite and said aqueous reaction mixture from step (2) is neutralized if necessary by the addition thereto of ammonium hydroxide to a pH of from 6.6 to 6.8.

9. The process of claim 6 further comprising neutralizing the aqueous reaction mixture from step (2) if necessary to a pH in the range of from 6.6 to 6.8 using a basic material selected from the group consisting of triethanolamine and ammonium hydroxide.

10. A process for making an aqueous solution of a fatty acid ester of ammonium isethionate comprising the steps of: (1) reacting ethylene oxide and ammonium bisulfite in an aqueous solution while (a) maintaining the pH in the range of from about 5.5 to about 6.5 by the controlled addition of an acid or base to the reaction mixture, and (b) maintaining the temperature in the range of from 25° C. to 85° C. to form an aqueous solution of ammonium isethionate; and (2) reacting said ammonium isethionate in the aqueous solution with at least one fatty acid to produce an aqueous solution of a fatty acid ester of ammonium isethionate having a content of fatty acid esters of ethylene glycol of less than 0.85% based on the weight of a 60% solution of the fatty acid ester of ammonium isethionate and wherein said aqueous solution resulting from step (2) is clear at ambient temperature.

11. A process according to claim 10 wherein said fatty acid comprises a coconut oil.

12. A process according to claim 10 wherein in step (2) said reaction of said ammonium isethionate and said fatty acid is conducted in the presence of an acidic catalyst.

13. The process of claim 12 comprising the additional step of neutralizing the aqueous reaction mixture from step (2) by adding a basic material selected from the group consisting of triethanolamine, ammonium hydroxide, and mixtures thereof, to adjust the pH to the range of from 6.6 to 6.8.

14. The process of claim 11 wherein said fatty acid is a composition comprised of, on a weight percent basis, 6% $C_{10}$, 49–51% $C_{12}$, 18–19% $C_{14}$, 9–10% $C_{16}$, 7% $C_{18:0}$, and 1–3% $C_{18:1}$, fatty acids.

15. The process of claim 12 wherein step (2) is carried out in the presence of a catalyst comprised of methanesulfonic acid and hypophosphorous acid.

16. The process of claim 12 wherein in step (1) said pH range is about 5.8 to about 6.2 and said temperature range is about 60° C. to about 65° C.

17. A process for making an aqueous solution of ammonium cocoyl isethionate which comprises the steps of: (1) adding sulfur dioxide and ethylene oxide to ammonia in an aqueous solution at a rate sufficient to maintain the temperature of said solution in the range of from about 60° C. to about 65° C. and while maintaining the pH of said solution in the range of from about 5.8 to about 6.2 by the controlled addition of an acid or base to the reaction mixture to form an aqueous solution of ammonium isethionate; and (2) reading said ammonium isethionate in said aqueous solution with coconut oil fatty acids in the presence of a catalyst comprised of methane sulfonic acid and hypophosphorous acid to produce an aqueous solution of ammonium cocoyl isethionate having a content of fatty acid esters of ethylene glycol of less than 0.85% based on the weight of a 60% solution of the ammonium cocoyl isethionate and wherein said aqueous solution resulting from step (2) is clear at ambient temperature.

18. The process of claim 17 comprising the additional step of neutralizing the reaction mixture from step (2), if necessary, with ammonium hydroxide to a pH of from 6.6. to 6.8.

* * * * *